United States Patent [19]

Jung

[11] Patent Number: 5,519,015
[45] Date of Patent: May 21, 1996

[54] CARBAPENEM ANTIBIOTIC COMPOUNDS

[75] Inventor: Frederic H. Jung, Rilly La Montagne, France

[73] Assignee: Zeneca Limited, London, United Kingdom

[21] Appl. No.: 142,459

[22] PCT Filed: Mar. 24, 1993

[86] PCT No.: PCT/GB93/00603

§ 371 Date: Nov. 26, 1993

§ 102(e) Date: Nov. 26, 1993

[87] PCT Pub. No.: WO93/19070

PCT Pub. Date: Sep. 30, 1993

[30] Foreign Application Priority Data

Mar. 26, 1992 [FR] France .................. 92 400836
Oct. 9, 1992 [FR] France .................. 92 402763

[51] Int. Cl.$^6$ .................. C07D 477/00; A61K 31/40
[52] U.S. Cl. .................. 514/210; 540/350
[58] Field of Search .................. 540/350; 514/210

[56] References Cited

U.S. PATENT DOCUMENTS 4,963,544 10/1990 Murata .
5,194,624 3/1993 Murata .
5,215,983 6/1993 Murata .

FOREIGN PATENT DOCUMENTS 0017992 10/1980 European Pat. Off. .
126587 11/1984 European Pat. Off. .
0160391 11/1985 European Pat. Off. .
0182213 5/1986 European Pat. Off. .
0243686 11/1987 European Pat. Off. .
0443883 8/1991 European Pat. Off. .
0472062 2/1992 European Pat. Off. .
60-233076 11/1985 Japan .
17481 10/1992 WIPO .

*Primary Examiner*—Rebecca Cook
*Attorney, Agent, or Firm*—Cushman Darby & Cushman

[57] ABSTRACT

The present invention relates to carbapenems and provides a compound of the formula (I)

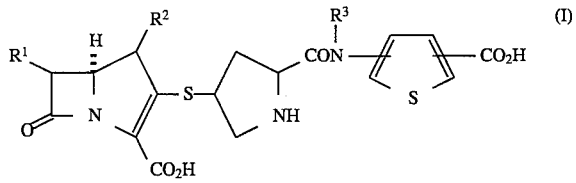

wherein:

$R^1$ is 1-hydroxyethyl, 1-fluoroethyl or hydroxymethyl;

$R^2$ is hydrogen or $C_{1-4}$alkyl;

$R^3$ is hydrogen or $C_{1-4}$alkyl; and the thienyl ring is optionally further substitued by one or two substituents selected from halo, cyano, $C_{1-4}$alkyl, nitro, hydroxy, carboxy, $C_{1-4}$alkoxy, trifluoromethyl, $C_{1-4}$alkoxycarbonyl, amino, $C_{1-4}$alkylamino, di-$C_{1-4}$alkylamino, sulfonic acid, $C_{1-4}$alkylS(O)$_n$— (wherein n is 0–2), $C_{1-4}$alkanoylamino, $C_{1-4}$alkanoyl(N-$C_{1-4}$alkyl)amino, carbamoyl, $C_{1-4}$alkylcarbamoyl, di-$C_{1-4}$alkylcarbamoyl and N-$C_{1-4}$alkanesulfonamido; or by a tetramethylene group attached to adjacent carbon atoms on the thienyl ring; or a pharmaceutically acceptable salt or in vivo hydrolysable ester thereof. Processes for their preparation, intermediates in their preparation, their use as therapeutic agents and pharmaceutical compositions containing them are also described.

12 Claims, No Drawings

CARBAPENEM ANTIBIOTIC COMPOUNDS

This application is a 371 of PCT/GB93/00603.

The present invention relates to carbapenems and in particular to such compounds containing a carboxy substituted thienyl group. This invention further relates to processes for their preparation, to intermediates in their preparation, to their use as therapeutic agents and to pharmaceutical compositions containing them. The compounds of this invention are antibiotics and can be used in the treatment of any disease that is conventionally treated with antibiotics for example in the treatment of bacterial infection in mammals including humans.

Carbapenems were first isolated from fermentation media in 1974 and were found to have broad spectrum antibacterial activity. Since this discovery substantial investigations have been made into new carbapenem derivatives and many hundreds of patents and scientific papers have been published.

The first, and so far the only, carbapenem to be commercially marketed is imipenem (N-formimidoyl thienamycin). This compound has a broad spectrum of antibacterial activity.

The present invention provides compounds with a broad spectrum of antibacterial activity including against both Gram positive and negative, aerobic and anaerobic bacteria. They exhibit good stability to beta-lactamases. In addition representative compounds of this invention exhibit favourable pharmacokinetics.

The carbapenem derivatives referred to herein are named in accordance with the generally accepted semi-systematic nomenclature:

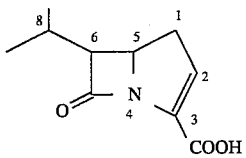

Accordingly the present invention provides a compound of the formula (I)

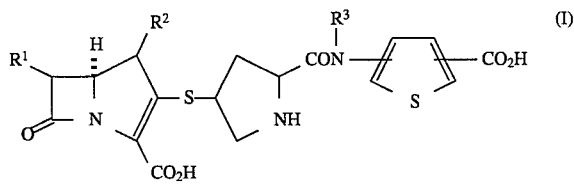

wherein:

$R^1$ is 1-hydroxyethyl, 1-fluoroethyl or hydroxymethyl;

$R^2$ is hydrogen or $C_{1-4}$alkyl;

$R^3$ is hydrogen or $C_{1-4}$alkyl; and the thienyl ring is optionally further substituted by one or two substituents selected from halo, cyano, $C_{1-4}$alkyl, nitro, hydroxy, carboxy, $C_{1-4}$alkoxy, trifluoromethyl, $C_{1-4}$alkoxycarbonyl, amino, $C_{1-4}$alkylamino, di-$C_{1-4}$alkylamino, sulfonic acid, $C_{1-4}$alkylS(O)$_n$— (wherein n is 0-2), $C_{1-4}$alkanoylamino, $C_{1-4}$alkanoyl(N-$C_{1-4}$alkyl)amino, carbamoyl, $C_{1-4}$alkylcarbamoyl, di-$C_{1-4}$alkylcarbamoyl and N-$C_{1-4}$alkanesulfonamido; or by a tetramethylene group attached to adjacent carbon atoms on the thienyl ring; or a pharmaceutically acceptable salt or in vivo hydrolysable ester thereof.

The term alkyl includes all straight and branched chain structures, for example, $C_{1-4}$alkyl includes n-butyl and 2-methylpropyl.

Preferably $R^1$ is 1-hydroxyethyl.

$R^2$ is hydrogen or $C_{1-4}$alkyl for example methyl, ethyl, n-propyl, 1-methylethyl and n-butyl.

Preferably $R^2$ is hydrogen or methyl. In particular $R^2$ is methyl.

$R^3$ is hydrogen or $C_{1-4}$alkyl for example methyl, ethyl, n-propyl, 1-methylethyl and n-butyl.

Preferably $R^3$ is hydrogen or methyl. In particular $R^3$ is hydrogen.

Suitable substituents for the thienyl ring include, for example:

for halo: fluoro, chloro, bromo and iodo;

for $C_{1-4}$alkyl: methyl, ethyl, propyl, 1-methylethyl, butyl and 2-methylpropyl;

for $C_{1-4}$alkoxy: methoxy, ethoxy, propoxy, 1-methylethoxy, butoxy and 2-methylpropoxy;

for $C_{1-4}$alkylcarbamoyl: methylcarbamoyl, ethylcarbamoyl and propylcarbamoyl;

for di-$C_{1-4}$alkylcarbamoyl: dimethylcarbamoyl and diethylcarbamoyl;

for $C_{1-4}$alkylamino: methylamino, ethylamino and propylamino;

for di-$C_{1-4}$alkylamino: dimethylamino, diethylamino and methylethylamino;

for $C_{1-4}$alkylS(O)$_n$—: methylthio, methylsulphinyl and methylsulphonyl;

for $C_{1-4}$alkanoylamino: acetamido and propionamido;

for $C_{1-4}$alkoxycarbonyl: methoxycarbonyl, ethoxycarbonyl and propoxycarbonyl;

for $C_{1-4}$alkanoyl(N$C_{1-4}$alkyl) amino: N-methylacetamido and N-ethylacetamido;

for N-$C_{1-4}$alkanesulfonamido: N-methanesulfonamido and N-ethanesulfonamido.

Preferably, when the thienyl ring is optionally substituted, the optional substituents are selected from halo, cyano, $C_{1-4}$alkyl, nitro, carboxy, hydroxy, $C_{1-4}$alkoxy, carbamoyl, amino, trifluoromethyl and tetramethylene.

Most preferably, the thienyl ring is not further substituted or further substituted by one hydroxy, methyl or tetramethylene group.

The present invention covers all epimeric, diastereoisomeric and tautomeric forms of the compounds of the formula (I) wherein the absolute stereochemistry at the 5-position is as illustrated in formula (I). When a bond is represented as a wedge, this indicates that in three dimensions the bond would be coming forward out of the paper and when a bond is represented as hatched, this indicates that in three dimensions the bond would be going back into the paper. The compounds of the formula (I) have a number of other stereocentres, namely: within the group $R^1$ (when $R^1$ is 1-hydroxyethyl or 1-fluoroethyl); at the 6-position; at the 1-position (when $R^2$ is $C_{1-4}$alkyl); and at the 2' and 4' positions in the pyrrolidine ring:

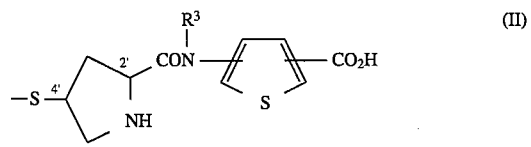

Preferred compounds are those in which the beta-lactam protons are in trans configuration with respect to one another. When $R^1$ is 1-hydroxyethyl or 1-fluoroethyl it is preferred that the 8-substituent has the R-configuration. Thus a preferred class of compounds is that of the formula (III):

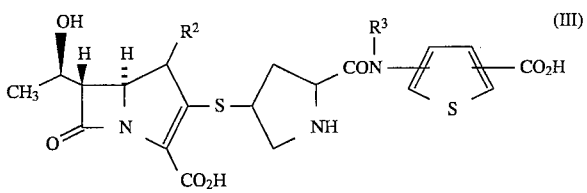

and pharmaceutically acceptable salts and in vivo hydrolysable esters thereof, wherein $R^2$, $R^3$ and optional substituents on the thienyl ring are as hereinbefore defined.

When $R^2$ is $C_{1-4}$alkyl, for example methyl, it is preferred that the compound is in the form of the 1R configuration.

Preferred compounds are those in which the pyrrolidine ring has the following absolute stereochemistry at the 2'- and 4'-positions:

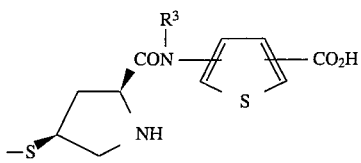

A suitable class of compounds of the present invention is that of the formula (IV):

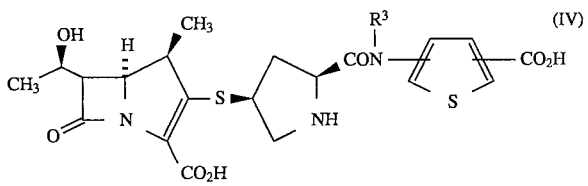

and pharmaceutically acceptable salts and in vivo hydrolysable esters thereof; wherein $R^3$ and optional substituents on the thienyl ring are as defined hereinbefore in formula (I).

In another aspect a suitable class of compounds are the compounds of the formula (IV) wherein $R^3$ is hydrogen, methyl or ethyl; and optional substituents on the thienyl ring are as defined hereinabove in formula (I).

In yet another aspect a suitable class of compounds is that of the compounds of the formula (IV) wherein the thienyl ring is optionally further substituted by one or two substituents selected from methyl, ethyl, hydroxy, carboxy, cyano, fluoro, chloro, bromo, carbamoyl, nitro, methoxy, ethoxy and propoxy; or by a tetramethylene group attached to adjacent carbon atoms on the thienyl ring; and $R^3$ is as defined hereinbefore in formula (I).

A particular class of compounds of the present invention is that of the formula (IV) wherein: $R^3$ is hydrogen or methyl;

and the thienyl ring is optionally further substituted by one substituent selected from methyl, ethyl, hydroxy, carboxy, cyano, chloro, bromo, nitro, methoxy, ethoxy and tetramethylene.

A preferred class of compounds of the present invention is that of the formula (IV) wherein: $R^3$ is hydrogen;

and the thienyl ring is optionally further substituted by one substituent selected from methyl, hydroxy, chloro, tetramethylene and carboxy.

A more preferred class of compounds of the present invention is that of the formula (IV) wherein: $R^3$ is hydrogen;

and the thienyl ring is either not further substituted or substituted by one substituent selected from methyl or hydroxy or by tetramethylene.

Particular compounds of the present invention are, for example, the following compounds of the formula (IV):

(1R,5S,6S,8R,2'S,4'S)-2-(2-(2-carboxy-4-thienylcarbamoyl)pyrrolidin- 4-ylthio)-6-(1-hydroxyethyl)-1-methylcarbapenem-3-carboxylic acid;

(1R,5S,6S,8R,2'S,4'S)-2-(2-(2-carboxy-3-thienylcarbamoyl)pyrrolidin- 4-ylthio)-6-(1-hydroxyethyl)-1-methylcarbapenem-3-carboxylic acid;

(1R,5S,6S,8R,2'S,4'S)-2-(2-(4-carboxy-2-thienylcarbamoyl)pyrrolidin- 4-ylthio)-6-(1-hydroxyethyl)-1-methylcarbapenem-3-carboxylic acid;

(1R,5S,6S,8R,2'S,4'S)-2-(2-(3-carboxy-2-(4,5,6,7 )-tetrahydrobenzo[b] -thienylcarbamoyl)pyrrolidin-4-ylthio)-6-(1-hydroxyethyl)-1 -methylcarbapenem-3-carboxylic acid;

(1R,5S,6S,8R,2'S,4'S)-2-(2-(3-carboxy-4-methyl-2 -thienylcarbamoyl)pyrrolidin- 4-ylthio)-6-(1-hydroxyethyl)-1-methylcarbapenem-3-carboxylic acid;

(1R,5S,6S,8R,2'S,4'S)-2-(2-(2-carboxy-5-thienylcarbamoyl)pyrrolidin- 4-ylthio)-6-(1-hydroxyethyl)-1-methylcarbapenem-3-carboxylic acid;

(1R,5S,6S,8R,2'S,4'S)-2-(2-(5-carboxy-3-hydroxy-2 -thienylcarbamoyl)pyrrolidin- 4-ylthio)-6-(1-hydroxyethyl)-1-methylcarbapenem-3-carboxylic acid;

and pharmaceutically acceptable salts and in vivo hydrolysable esters thereof.

Suitable pharmaceutically acceptable salts include acid addition salts such as hydrochloride, hydrobromide, citrate, maleate and salts formed with phosphoric and sulfuric acid. In another aspect suitable salts are base salts such as an alkali metal salt for example sodium or potassium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or aminoacids, for example, lysine.

For the avoidance of doubt there may be one, two, three or four salt-forming cations dependent on the number of carboxylic acid functions and valency of said cations.

Preferred pharmaceutically acceptable salts are sodium and potassium salts. However, to facilitate isolation of the salt during preparation, salts which are less soluble in the chosen solvent may be preferred, whether pharmaceutically acceptable or not.

In vivo hydrolysable esters are those pharmaceutically acceptable esters that hydrolyse in the human body to produce the parent hydroxy or carboxy compound. Such esters can be identified by administering, e.g. intravenously to a test animal, the compound under test and subsequently examining the test animal's body fluids. Suitable in vivo hydrolysable ester forming groups for hydroxy include acetyl, propionyl, pivaloyl, $C_{1-4}$alkoxycarbonyl for example ethoxycarbonyl and phenylacetyl. Suitable in vivo hydrolysable esters for carboxy include $C_{1-6}$alkoxymethyl esters for example methoxymethyl; $C_{1-6}$alkanoyloxymethyl esters for example pivaloyloxymethyl; $C_{3-8}$ cycloalkoxycarbonyloxy$C_{1-6}$alkyl, for example 1-cyclohexyloxycarbonyloxyethyl; 1,3-dioxolen-2-onylmethyl esters for example 5-methyl-1,3-dioxolen-2-onylmethyl; phthalidyl esters and $C_{1-6}$alkoxycarbonyloxyethyl esters for example 1-methoxycarbonyloxyethyl and may be formed at any carboxy group in the compounds of this invention.

In order to use a compound of the formula (I) or a pharmaceutically acceptable salt or in vivo hydrolysable ester thereof for the therapeutic treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt or in vivo hydrolysable ester thereof and a pharmaceutically acceptable carrier.

The pharmaceutical compositions of this invention may be administered in standard manner for the disease condition that it is desired to treat, for example by oral, rectal or parenteral administration. For these purposes the compounds of this invention may be formulated by means known in the art into the form of, for example, tablets, capsules, aqueous or oily solutions or suspensions, emulsions, dispersible powders, suppositories and sterile injectable aqueous or oily solutions or suspensions.

The compounds of the present invention may be formulated as dry powder filled vials, which may contain the compound of the present invention alone or as a dry blended mixture. For example an acidic compound of the present invention may be dry blended with an alkali metal carbonate or bicarbonate. Freeze dried formulations of compounds of the present invention, alone or as a mixture with standard excipients, are possible. Standard excipients include structure formers, cryoprotectants and pH modifiers, such as, mannitol, sorbitol, lactose, glucose, sodium chloride, dextran, sucrose, maltose, gelatin, bovine serum albumin (BSA), glycine, mannose, ribose, polyvinylpyrrolidine (PVP), cellulose derivatives, glutamine, inositol, potassium glutamate, erythritol, serine and other amino acids and buffer agents e.g. disodium hydrogen phosphate and potassium citrate.

In addition to the compounds of the present invention the pharmaceutical composition of this invention may also contain, or be co-administered with, one or more known drugs selected from other clinically useful antibacterial agents (for example other beta-lactams or aminoglycosides), inhibitors of beta-lactamase (for example clavulanic acid), renal tubular blocking agents (e.g. probenecid) and inhibitors of metabolising enzymes (for example inhibitors of dehydropeptidases, for example Z-2-acylamino-3-substituted propenoates such as cilastatin) and N-acylated amino acids such as betamipron (also see EP-A-178911).

A suitable pharmaceutical composition of this invention is one suitable for oral administration in unit dosage form, for example a tablet or capsule which contains between 100 mg and 1 g of the compound of this invention.

A preferred pharmaceutical composition of the invention is one suitable for intravenous, subcutaneous or intramuscular injection, for example a sterile injectable composition containing between 1 and 50% w/w of the compound of this invention.

Specific examples of compositions, which are constituted as a 1% solution in water, freeze dried and may be made up by adding 0.9% aqueous sodium chloride solution to give the required concentration, preferably 1 mg–10 mg/ml, are as follows:

| Composition 1 | |
|---|---|
| Compound of Example 1 | 50 mg |
| Composition 2 | |
| Compound of Example 1 | 50 mg |
| Glycine | 31 mg |

Further specific examples of compositions are as above, but where the compound of example 1 is replaced by any one of examples 2 to 7.

The pharmaceutical compositions of the invention will normally be administered to man in order to combat infections caused by bacteria, in the same general manner as that employed for imipenem due allowance being made in terms of dose levels for the pharmacokinetics of the compound of the present invention relative to the clinical use of imipenem. Thus each patient will receive a daily intravenous, subcutaneous or intramuscular dose of 0.05 to 5 g, and preferably 0.1 to 2.5 g, of the compound of this invention, the composition being administered 1 to 4 times per day, preferably 1 or 2 times a day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose. Thus a suitable daily oral dose is 0.05 to 5 g. of the compound of this invention, the composition being administered 1 to 4 times per day.

In a further aspect the present invention provides a process for preparing the compounds of the formula (I) or a pharmaceutically acceptable salt or in vivo hydrolysable ester thereof which process comprises deprotecting a compound of the formula (V) wherein the thienyl ring is optionally further substituted as in formula (I):

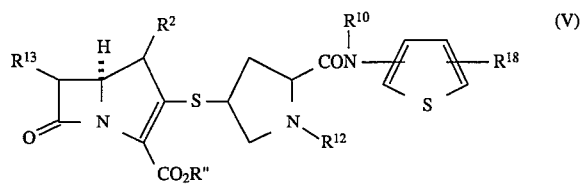

wherein $R^2$ is as hereinbefore defined; $R^{10}$ is a group $R^3$ or an amino protecting group; $R^{13}$ is a group $R^1$, protected hydroxymethyl or 1-(protected hydroxy)ethyl; $R^{11}$ is hydrogen or a carboxy protecting group; $R^{12}$ is hydrogen or an amino protecting group, $R^{18}$ is carboxy or a protected carboxy group and wherein any optional substituent on the thienyl ring is optionally protected; and wherein at least one protecting group is present; and thereinafter if necessary;

(i) forming a pharmaceutically acceptable salt, (ii) esterifying to form an in vivo hydrolysable ester.

Protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

The compounds of the formula (V) are novel and form another aspect of the invention.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or araliphatic alcohol or of an ester-forming silanol (the said alcohol or silanol preferably containing 1–20 carbon atoms).

Examples of carboxy protecting groups include straight or branched chain (1–12C)alkyl groups (e.g. isopropyl, t-butyl); lower alkoxy lower alkyl groups (e.g. methoxymethyl, ethoxymethyl, isobutoxymethyl); lower aliphatic acyloxy lower alkyl groups, (e.g. acetoxymethyl, propionyloxymethyl, butyryloxymethyl, pivaloyloxymethyl); lower alkoxycarbonyloxy lower alkyl groups (e.g. 1-methoxycarbonyloxyethyl, 1-ethoxycarbonyloxyethyl); aryl lower alkyl groups (e.g. p-methoxybenzyl, o-nitrobenzyl, p-nitrobenzyl, benzhydryl and phthalidyl); tri(lower alkyl)silyl groups (e.g. trimethylsilyl and t-butyldimethylsilyl); tri(lower alkyl)silyl lower alkyl groups (e.g. trimethylsilylethyl); diaryl(lower alkyl)silyl groups (e.g. t-butyldiphenylsilyl); and (2–6C)alkenyl groups (e.g. allyl and vinylethyl).

Methods particularly appropriate for the removal of carboxyl protecting groups include for example acid-, base-, metal- or enzymically-catalysed hydrolysis, for groups such as p-nitrobenzyloxycarbonyl, hydrogenation and for groups such as o-nitrobenzyloxycarbonyl, photolytically.

Examples of hydroxy protecting groups include lower alkenyl groups (e.g. allyl); lower alkanoyl groups (e.g. acetyl); lower alkoxycarbonyl groups (e.g. t-butoxycarbonyl); lower alkenyloxycarbonyl groups (e.g. allyloxycarbonyl); aryl lower alkoxycarbonyl groups (e.g. benzoyloxycarbonyl, p-methoxybenzyloxycarbonyl, o-nitrobenzyloxycarbonyl, p-nitrobenzyloxycarbonyl); tri lower alkylsilyl (e.g. trimethylsilyl, t-butyldimethylsilyl); diaryl(lower alkyl)silyl (e.g. t-butyldiphenylsilyl) and aryl lower alkyl (e.g. benzyl) groups.

Examples of amino protecting groups include formyl, aralkyl groups (e.g. benzyl and substituted benzyl, e.g. p-methoxybenzyl, nitrobenzyl and 2,4-dimethoxybenzyl, and triphenylmethyl); di-p-anisylmethyl and furylmethyl groups; lower alkoxycarbonyl (e.g. t-butoxycarbonyl); lower alkenyloxycarbonyl (e.g. allyloxycarbonyl); aryl lower alkoxycarbonyl groups (e.g. benzyloxycarbonyl, p-methoxybenzyloxycarbonyl, o-nitrobenzyloxycarbonyl, p-nitrobenzyloxycarbonyl); trialkylsilyl (e.g. trimethylsilyl and t-butyldimethylsilyl); diaryl(lower alkyl)silyl (e.g. t-butyldiphenylsilyl); alkylidene (e.g. methylidene); benzylidene and substituted benzylidene groups.

Methods appropriate for removal of hydroxy and amino protecting groups include, for example, acid-, base-, metal- or enzymically-catalysed hydrolysis, for groups such as p-nitrobenzyloxycarbonyl, hydrogenation and for groups such as o-nitrobenzyloxycarbonyl, photolytically.

Preferred protecting groups for carboxy and hydroxy groups in compounds of the formula (I) are the groups allyl and p-nitrobenzyl. A preferred method for removal of the allyl group is by palladium catalysis using tetrakis(triphenylphosphine)palladium and Meldrum's acid, in DMF or a dipolar aprotic solvent tetrahydrofuran mixture, such as dimethylsulfoxide/tetrahydrofuran or 1,3-dimethyl-2-oxotetrahydropyrimidine/tetrahydrofuran, or an alcohol/tetrahydrofuran mixture such as isopropanol/tetrahydrofuran or ethanol/tetrahydrofuran, preferably at ambient temperature. Alternatively, methylaniline may be used in place of Meldrum's acid, in dichloromethane. These conditions allow isolation of the product by precipitation of the sodium salt on the addition of a sodium salt such as sodium 2-ethylhexanoate.

A preferred method for removal of the p-nitrobenzyl group is hydrogenation using a palladium catalyst.

In another aspect of the present invention the compounds of the formulae (I) and (V) may be prepared by a) reacting compounds of the formulae (VI) and (VII):

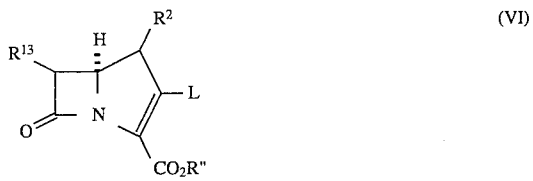

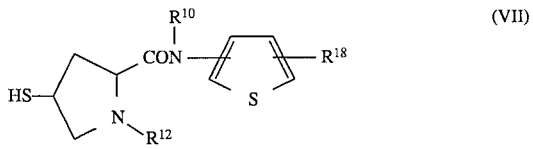

wherein $R^2$, $R^{10}$, $R^{11}$, $R^{12}$, $R^{13}$ and $R^{18}$ are as hereinbefore defined, optional substituents on the thienyl ring are as hereinbefore defined and L is a leaving group, or b) cyclising a compound of the formula (VIII):

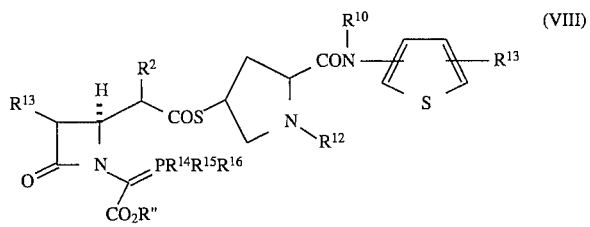

wherein $R^2$, $R^{10}$, $R^{11}$, $R^{12}$, $R^{13}$ and $R^{18}$ are as hereinbefore defined, optional substituents on the thienyl ring are as hereinbefore defined and $R^{14}$, $R^{15}$ and $R^{16}$ are independently selected from $C_{1-6}$alkoxy, aryloxy, di-$C_{1-6}$alkylamino and diarylamino or any two of $R^{14}$–$R^{16}$ represent o-phenylenedioxy or one of $R^{14}$–$R^{16}$ is $C_{1-4}$alkyl, allyl, benzyl or phenyl, and the other two values are independently selected from $C_{1-4}$alkyl, trifluromethyl or phenyl, wherein any phenyl group is optionally substituted with $C_{1-3}$alkyl or $C_{1-3}$alkoxy; and wherein any functional group is optionally protected and thereinafter if necessary:

(i) removing any protecting groups;

(ii) forming a pharmaceutically acceptable salt;

(iii) esterifying to form an in vivo hydrolysable ester,

Suitably in the compound of the formula (VI), L is the reactive ester of a hydroxy group such as a sulfonate (for example $C_{1-6}$alkanesulfonyloxy, trifluoromethanesulfonyloxy, benzenesulfonyloxy, toluenesulfonyloxy), a phosphoric ester (for example a diarylphosphoric ester such as diphenylphosphoric ester) or L is a halide (for example chloride). In an alternative L is a sulfoxide for example —SOCH=CH—NHCOCH$_3$ which may be readily displaced. Preferably L is diphenylphosphoric ester (—OP(O)(OPh)$_2$).

Compounds of the formula (VI) and their preparation are well known in the carbapenem literature, for example see EP-A-126587, EP-A-160391, EP-A-243686 and EP-A-343499.

The reaction between the compounds of the formulae (VI) and (VII) is typically performed in the presence of a base such as an organic amine for example di-isopropylethylamine or an inorganic base for example an alkali metal carbonate such as potassium carbonate. The reaction is conveniently performed at a temperature between −25° C. and ambient, suitably at about 4° C. The reaction is generally performed in an organic solvent such as acetonitrile or dimethylformamide. The reaction is generally performed in a manner similar to that described in the literature for similar reactions.

The compounds of the formula (VII) are novel and form another aspect of the present invention.

The compounds of the formula (VII) may be prepared by the deprotection of a compound of the formula (IX):

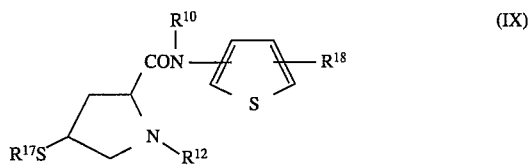
(IX)

wherein $R^{10}$, $R^{12}$ and $R^{18}$ are as hereinbefore defined, optional substituents on the thienyl ring are as hereinbefore defined and $R^{17}$ is a protecting group, for example $C_{1-6}$alkanoyl, $C_{1-6}$alkoxycarbonyl or benzoyl. Preferred values for $R^{17}$ are acetyl and t-butoxycarbonyl. The compounds of the formula (IX) can be converted to the compounds of the formula (VII) by standard methods of deprotection, for example acetyl groups can be removed by basic hydrolysis in aqueous alkanol, alkenol, for example allyl alcohol, or tetrahydrofuran.

The compounds of the formula (IX) are novel and form another aspect of the present invention.

The compounds of the formula (IX) may be prepared by the reaction of an activated derivative of a compound of the formula (X), which may be formed in situ, with a compound of the formula (XI):

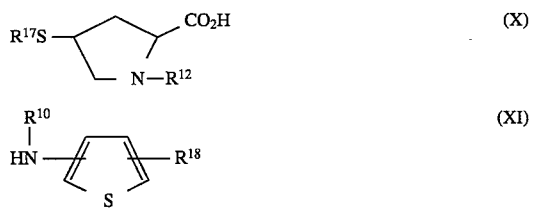

wherein $R^{10}$, $R^{12}$, $R^{17}$ and $R^{18}$ are as hereinbefore defined and optional substituents on the thienyl ring are as hereinbefore defined. Activated derivatives of the compound of the formula (X) include acid halides, anhydrides and 'activated' esters such as 1H-benzo[1,2,3]-triazol-1-yl, pentafluorophenyl and 2,4,5-trichlorophenyl esters or the benzimidazol-2-yl ester of the thiocarboxylic acid corresponding to (X). The reaction of the compounds of the formulae (X) and (XI) is performed under standard methods, for example in the presence of sulfonyl chloride at ambient temperature.

The compounds of the formulae (X) and (XI) are prepared by standard methods known to the skilled chemist such as the methods the Examples hereinafter, the methods described in EP-A-126587 or by methods analogous or similar thereto.

Suitably, in the compounds of the formula (VIII), $R^{14}$, $R^{15}$ and $R^{16}$ are independently selected from $C_{1-6}$ alkoxy such as methoxy, ethoxy, isopropoxy, n-propoxy or n-butoxy; aryloxy such as optionally substituted phenoxy; di-$C_{1-6}$alkylamino such as dimethylamino or diethylamino; diarylamino such as diphenylamino or any two of $R^{14}$–$R^{16}$ represent o-phenylenedioxy. Preferably each of $R^{14}$–$R^{16}$ have the same value and are $C_{1-6}$alkoxy for example methoxy, ethoxy, isopropoxy or n-butoxy or are phenoxy.

The compounds of the formula (VIII) are cyclized under conventional conditions known in the art to form compounds of the formula (V). Typical conditions are heating in a substantially inert organic solvent such as toluene, xylene or ethyl acetate at temperatures in the region 60°–150° C. Typically the reaction is performed in an atmosphere of nitrogen and is carried out in the presence of a radical scavenger for example hydroquinone.

The compounds of the formula (VIII) may be formed and cyclized in situ. The compounds of the formula (VIII) may conveniently be prepared by reacting compounds of the formulae (XII) and (XIII):

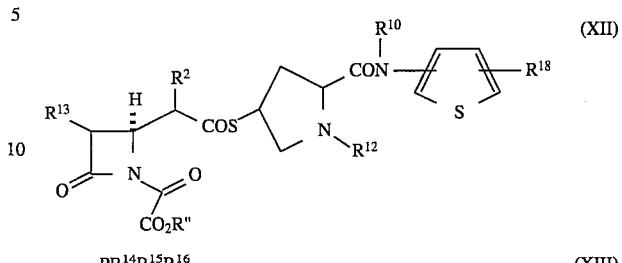
(XII)

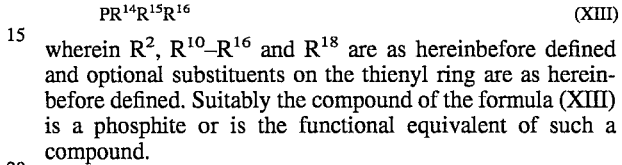
$PR^{14}R^{15}R^{16}$ (XIII)

wherein $R^2$, $R^{10}$–$R^{16}$ and $R^{18}$ are as hereinbefore defined and optional substituents on the thienyl ring are as hereinbefore defined. Suitably the compound of the formula (XIII) is a phosphite or is the functional equivalent of such a compound.

The reaction between the compounds of the formulae (XII) and (XIII) is conveniently performed in an organic solvent such as toluene, xylene, ethyl acetate, chloroform, dichloromethane, acetonitrile or dimethylformamide. Typically the reaction is carried out at an elevated temperature for example 60°–150° C.

The compounds of the formula (XII) may be prepared by a number of methods known in the art. For example the compounds of the formula (XII) may be prepared by the acylation of a compound of the formula (XIV):

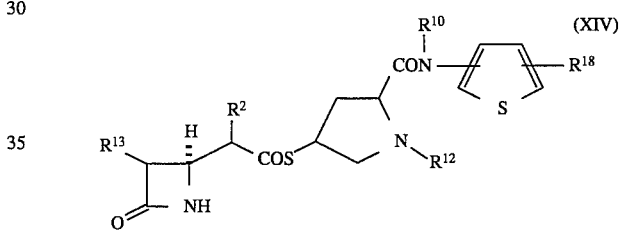
(XIV)

wherein $R^2$, $R^{10}$, $R^{12}$, $R^{13}$, and $R^{18}$ are as hereinbefore defined and optional substituents on the thienyl ring are as hereinbefore defined with a compound of the formula (XV):

Cl—CO—COOR¹¹ (XV)

wherein $R^{11}$ is as hereinbefore defined.

The compounds of the formula (XIV) may be prepared by reacting compounds of the formulae (XVI) and (VII):

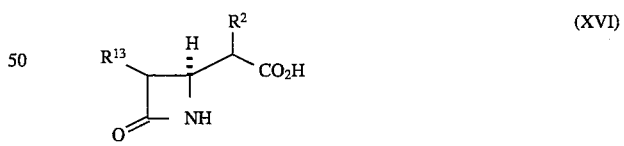
(XVI)

wherein $R^2$ and $R^{13}$ are as hereinbefore defined. The compounds of the formula (XVI) are known in the art and may be reacted with the compounds of the formula (VII) under conventional acylation methods known in the art.

Compounds of the formulae (VII), (XII) and (XIV) are novel and, as such, form another aspect of this invention.

The following biological test methods, data and Examples serve to illustrate the present invention.

Antibacterial Activity

The pharmaceutically acceptable carbapenem compounds of the present invention are useful antibacterial agents having a broad spectrum of activity in vitro against standard laboratory microorganisms, both Gram-negative and Gram-positive, which are used to screen for activity against pathogenic bacteria. The antibacterial spectrum and potency of a particular compound may be determined in a standard test system. In particular the carbapenems of the present invention show good stability to beta-lactamases and have a particularly good elimination half life in mammals. In general compounds show significant improvement over imipenem.

The antibacterial properties of the compounds of the invention may also be demonstrated in vivo in conventional tests.

Carbapenem compounds have generally been found to be relatively non-toxic to warm-blooded animals, and this generalisation holds true for the compounds of the present invention. Compounds representative of the present invention were administered to mice at doses in excess of those required to afford protection against bacterial infections, and no overt toxic symptoms or side effects attributable to the administered compounds were noted.

The following results were obtained for representative compounds on a standard in vitro test system using Diagnostic Sensitivity Test. The antibacterial activity is described in terms of the minimum inhibitory concentration (MIC) determined by the agar-dilution technique with an inoculum size of $10^4$ CFU/spot.

| ORGANISM | MIC (µg/ml) EXAMPLE 1 |
|---|---|
| S. aureus Oxford | 0.125 |
| E. coli DCO | 0.008 |
| P. morganii I+001 | 0.008 |
| Enterobacter cloacae P99- | 0.008 |
| B. fragilis AMP S | 0.125 |

In the following examples, which are representative of the scope:

(a) NMR spectra were taken at 200 MHz or 400 MHz unless otherwise stated;

(b) Allyloxy means the propen-1-yloxy group —OCH$_2$CH=CH$_2$;

(c) THF means tetrahydrofuran;

(d) DMF means dimethylformamide;

(e) DMSO means dimethylsulphoxide;

(f) Evaporation of solvents was carried out under reduced pressure;

(g) HPLC means high pressure liquid chromatography;

(h) Temperatures are in degrees centigrade.

(i) TFA means trifluoroacetic acid; and (j) tlc means thin layer chromatography.

EXAMPLE 1

(1R,5S,6S,8R,2'S,4'S)-2-(2-(2-Carboxy-4-thienylcarbamoyl)pyrrolidin- 4-ylthio)-6-(1-hydroxyethyl)-1-methylcarbapenem-3-carboxylic acid (dipotassium salt).

A solution of 4-nitrobenzyl (1R,5S,6S,8R,2'S,4'S)-2-(1-(4 -nitrobenzyloxycarbonyl)-2-(2-carboxy-4-thienylcarbamoyl)pyrrolidin- 4-ylthio)-6-(1-hydroxyethyl)-1-methylcarbapenem-3-carboxylate (diisopropylethylamine salt) (equivalent to 250 mg of free acid, 0.31 mM) in water (10 ml) and potassium bicarbonate (65 mg, 0.629 mM) was hydrogenated at atmospheric pressure in the presence of palladium/carbon (10%) (200 mg). The reaction was followed by analytical HPLC. At the end of the reaction the catalyst was removed by filtration, and the residual solution purified by preparative HPLC (Nucleosil C-18, 10 µM, diameter 2.4 cm; length 25 cm). Using water as the eluant the fractions containing the required compound were concentrated and lyophilised to give the title compound (65 mg, 37%).

NMR (DMSO-d$_6$+AcOD-d$_4$): δ1.15 (2d, 2H); 1.75 (m, 1H); 2.65 (m, 1H); 2.82 (m, 1H); 3.2 (dd, 1H); 3.3–3.5 (m, 2H); 3.65 (m, 1H); 3.85–4.05 (m, 2H); 4.15 (dd, 1H); 7.72 (s, 1H); 7.78 (s, 1H).

The starting material was prepared as follows:

4-Nitro-2-thiophenecarboxylic acid

2-Thiophenecarboxylic acid (6.4 g, 50 mM) was suspended in acetic anhydride (15 ml) and fuming nitric acid (16 ml) in glacial acetic acid (25 ml) added slowly over 1 hour with stirring, while keeping the temperature of the reaction mixture below 30° C. The reaction mixture was stirred at ambient temperature for 2 hours. The product was purified by subjecting to chromatography (470 ml) on HP20SS resin using methanol/(water+1% acetic acid): 0/100→50/50 as eluant. The pure title compound was obtained (1.3 g) together with a mixture of 4- and 5-nitrothiophene-2-carboxylic acid (4.4 g).

NMR (CDCl$_3$): δ8.35 (d, 1H); 8.5 (d, 1H).

4-Amino-2-thiophenecarboxylic acid

4-Nitro-2-thiophenecarboxylic acid (1 g, 5.7 mmol) was added with stirring to a solution of SnCl$_2$. 2H$_2$O (3.25 g, 14.4 mmol) in concentrated HCl (10 ml). The mixture was stirred for 6 hours at ambient temperature and purified by subjecting to chromatography on HP20SS resin, using water as eluant, to give the title compound (0.59 g, 71%).

NMR (DMSO-d$_6$+AcOD-d$_4$): δ7.6 (s, 2H).

(2S,4S)-1-(4-Nitrobenzylcarbonyl)-2-(2-carboxy-4-thienylcarbamoyl)pyrrolidin- 4-ylthioacetate.

(2S,4S)-4-Acetylthio-2-carboxy-1-(4-nitrobenzyloxycarbonyl)pyrrolidine (1.5 g, 4.08 mmol) was dissolved at ambient temperature in thionyl chloride (10 ml). The mixture was stirred for 4 hours at ambient temperature. The thionyl chloride was evaporated, the residual oil taken up in dichloromethane/toluene (10 ml, 1:1) and the solvent removed by evaporation. The residual oil was dried under vacuum for 1 hour and dissolved in dichloromethane (25 ml). This solution was added to a mixture of 4-amino-2-thiophenecarboxylic acid (0.58 g, 4.08 mmol), trimethylsilyl chloride (1 ml, 8.2 mmol) and diisopropylethylamine (3 ml, 17.25 mmol) in dichloromethane (40 ml) at 0°. The reaction mixture was stirred for 12 hours at ambient temperature, the solvent evaporated and the residue dissolved in DMF and subjected to chromatography on HP20SS resin, eluting with acetonitrile/water/acetic acid (40:60:1), followed by concentration and lyophilisation to give the title compound (0.84 g, 42%).

NMR (DMSO-d$_6$+AcOD-d$_4$): δ1.92 (m, 1H), 2.32 (s, 3H), 2.76 (m, 1H), 3.35 (m, 1H); 3.9–4.2 (m, 2H); 4.42 (m, 1H); 5.0–5.35 (m, 2H); 7.45 (d, 1H); 7.65 (d, 1H); 7.76 (s, 2H); 7.96 (d, 1H); 8.22 (d, 1H).

(2S,4S)-1-(4-Nitrobenzyloxycarbonyl)-2-(2-carboxy-4-thienylcarbamoyl)pyrrolidin- 4-ylthiol.

(2S,4S)-1-(4-Nitrobenzyloxycarbonyl-2-(2-carboxy-4-thienylcarbamoyl)pyrrolidin- 4-ylthioacetate (0.475 g, 0.963 mmol) was dissolved in a mixture of dioxane/water (1:1) (20 ml) and treated with a 1M aqueous solution of NaOH (2.5 ml, 2.4 mmol). The reaction was monitored by HPLC. After 1 hour, the pH was adjusted to pH3 with a 6M aqueous solution of HCl, at 0°. The reaction mixture then was evaporated and dried under vacuum for 1 hour.

4-Nitrobenzyl (1R,5R,6S,8R,2'S,4'S)-2-(1-(4-nitrobenzyloxycarbonyl)- 2-(2-carboxy-4-thienylcarbamoyl)pyrrolidin-4-ylthio)-6-(1-hydroxyethyl)- 1-methylcarbapenem-3carboxylate (diisopropylethylamine salt)

A solution of 4-nitrobenzyl (1R,5R,6S,8R)-6-(1-hydroxyethyl)- 1-methyl-2-diphenylphosphoryloxycarbapenem-3-carboxylate (0.575 g, 0.968 mmol) in DMF (5 ml) was added to a solution of (2S,4S)-1-(4 -nitrobenzyloxycarbonyl)-2-(2-carboxy-4-thienylcarbamoyl)pyrrolidin-4-ylthiol in DMF (5 ml). Diisopropylethylamine (0.505 ml, 2.9 mmol), tri-n-butylphosphine (0.24 ml, 0.968 mmol) and water (20 μl, 0.968 mmol) were added to the reaction mixture, which was stirred at 4° C. for 14 hours. The title compound was purified by subjecting to chromatgraphy on HP20SS resin (100 ml) using acetonitrile/water (30:70) as the eluant. Evaporation and lyophilisation gave the title compound (0.375 g, 49%).

NMR (DMSO-$d_6$+AcOD-$d_4$): δ1.15 (t, 15H); 1.25 (2d, 6H); 1.95 (m, 1H); 2.81 (m, 1H); 3.15 (q, 2H); 3.3 (m, 1H); 3.42 (m, 1H); 3.5–3.7 (m, 3H); 3.9–4.2 (m, 3H); 4.2–4.35 (m, 1H); 4.35–4.55 (m, 1H); 5.15–5.45 (m, 4H); 7.35–8.05 (m, 8H); 8.15 (s, 1H); 8.18 (s, 1H).

EXAMPLE 2

(1R,5S,6S,8R,2'S,4'S)-2-(2-Carboxy-3-thienylcarbamoyl)pyrrolidin-4 -ylthio )-6-(1-hydroxyethyl)-1-methylcarbapenem-3-carboxylic acid (dipotassium salt).

A solution of allyl (1R,5S,6S,8R,2'S,4'S)-2-(1-(4-nitrobenzyloxycarbonyl)- 2-(2-carboxy-3-thienylcarbamoyl)pyrrolidin-4 -ylthio)-6-(1-hydroxyethyl)-1-methylcarbapenem-3-carboxylate diisopropylethylamine salt (equivalent to 0.49 g of the free acid, 0.7 mmol) in THF (25 ml) was treated with triphenylphosphine (20 mg, 0.076 mmol), potassium hexanoate (0.46M solution in ethyl acetate, 3.2 ml, 1.47 mmol), hexanoic acid (0.235 ml, 1.47 mmol) and tetrakis(triphenylphosphine)palladium (70 mg) for 1 hour at ambient temperature. Ethyl acetate (25 ml) was then added to the reaction mixture and the precipitate collected by filtration. The precipitate was washed with ethyl acetate and dried (0.45 g, 87%). This crude product was dissolved in water (10 ml) and hydrogenated at atmospheric pressure over palladium/carbon (10%, 0.35 g). The deprotection was followed by analytical HPLC. At the end of the reaction (usually 0.5 to 1 hour), the catalyst was filtered off, and the filtrate concentrated and purified by subjecting to preparative chromatography (Nucleosil C-18), using water as the eluant, to give the title compound, after concentration and lyophilisation of the required fractions (0.13 g, 38%).

NMR (DMSO-$d_6$+AcOD-$d_4$): δ1.15 (2d, 6H); 1.75 (m, 1H); 2.5–2.7 (m, 2H); 3.18 (dd, 1H); 3.2–3.65 (m, 3H); 3.9–4.05 (m, 2H); 4.15 (dd, 1H); 7.55 (d, 1H); 7.98 (d, 1H).
(2S,4S)-1-(4-Nitrobenzyloxycarbonyl)-2-(2-carboxy-3-thienylcarbamoyl)pyrrolidin- 4-ylthioacetate.

The title compound was prepared from 3-nitro-2-thiophenecarboxylic acid using a similar method to that of example 1, except no silylation was necessary. The amino acid was solubilized in dichloromethane with diisopropylethyl amine.

NMR (DMSO-$d_6$+AcOD-$d_4$, TFA-d): δ2.15 (m, 1H); 2.27 (s, 3H); 2.85 (m, 1H); 3.4 (m, 1H); 3.85–4.3 (m, 2H); 4.53 (dd, 1H); 5.22 (d, 2H); 7.5 (d, 2H); 7.75 (d, 1H); 7.92 (d, 1H); 8.05 (d, 2H).
Allyl (1R,5S,6S,2'S)-2-(1-(4-nitrobenzyloxycarbonyl)-2-(2 -carboxy-3-thienylcarbamoyl)pyrrolidin-4-ylthio)-6-(1-hydroxyethyl)- 1-methylcarbapenem-3-carboxylate (diisopropylethylamine salt).

The title compound was prepared from (2S,4S)-1-(4-nitrobenzylcarbonyl)- 2-(2-carboxy-3-thienylcarbamoyl)pyrrolidin-4-ythiol and allyl (1R,5R,6S,8R)-6-(1-hydroxyethyl)-1-methyl-2-diphenylphosphoryloxycarbapenem- 3-carboxylate using a similar method to that of example 1.

NMR (DMSO-$d_6$+AcOD-$d_4$): δ1.15 (s, 15H); 1.3 (2d, 6H); 2.05 (m, 1H); 2.88 (m, 1H); 3.15 (q, 2H); 3.25 (dd, 1H); 3.32–3.58 (m, 2H); 3.62 (qi, 2H); 3.9–4.05 (m, 2H); 4.05–4.3 (m, 2H); 4.4–4.65 (m, 3H); 5.0–5.4 (m, 4H); 5.85 (m, 1H); 7.45 (d, 1H); 7.64 (d, 1H); 7.7 (d, 1H); 7.85–8.02 (m, 2H); 8.25 (d, 1H).

EXAMPLE 3

(1R,5S,6S,8R,2'S,4'S)-2-(2-(4-Carboxy-2-thienylcarbamoyl)pyrrolidin- 4-ylthio)-6-(1-hydroxyethyl)-1-methylcarbapenem-3-carboxylic acid (dipotassium salt).

The title compound was prepared from allyl (1R,5S,6S, 8R,2'S,4'S)- 2-(1-(4-nitrobenzyloxycarbonyl)-2-(4-allyloxycarbonyl-2-thienylcarbamoyl)pyrrolidin- 4-ylthio)-6-(1-hydroxyethyl)-1-methylcarbapenem- 3-carboxylate diisopropylethylamine salt using a similar method to that of example 2.

NMR (DMSO-$d_6$+AcOD-$d_4$): δ1.16 (2×d, 6H); 1.67 (m, 1H); 2.55 (m, 1H); 2.64 (m, 1H); 3.2 (dd, 1H); 3.39–3.43 (m, 2H); 3.60 (m, 1H); 3.93–3.97 (m, 2H); 4.15 (dd, 1H); 7.15 (s, 1H); 7.67 (s, 1H).
Allyl 2-nitro-4-thiophenecarboxylate 2-Nitro-4-thiophenecarboxylic acid (2.5 g, 14.45 mmol) was suspended in DMF (25 ml) in the presence of potassium carbonate (4 g, 28.9 mmol) at ambient temperature. Allyl bromide (5 ml, 57.8 mmol) was added to this solution and the mixture stirred at ambient temperature overnight. The mixture was diluted with water and extracted with ethyl acetate. After concentration, the residue was purified by silica gel chromatography using ethyl acetate/petroleum ether as eluant (10:30) to give the title compound (2.45 g, 77%).

NMR (CDCl$_3$): δ4.78 (m, 1H); 4.80 (m, 1H); 5.25 (m, 1H); 5.45 (d, 1H); 6.0 (m, 1H); 8.25 (d, 1H); 8.75 (d, 1H).
Allyl 2-amino-4-thiophenecarboxylate Allyl 2-nitro-4-thiophenecarboxylate was suspended in concentrated HCl (25 ml), at 0°. SnCl$_2$.2H$_2$O (7.44 g, 32.36 mmol) was added and after stirring for 4 hours at ambient temperature the pH was adjusted to 10 with NaOH. Extraction with ethyl acetate and purification by subjecting to flash silica gel chromatography using ethyl acetate/petroleum ether as eluant (25:75), gave the title compound (1.15 g, 55%).

NMR (CDCl$_3$): δ3.75 (m, 2H); 4.65 (m, 1H); 4.72 (m, 1H); 5.2 (m, 1H); 5.35 (d, 1H); 6. (m, 1H); 6.57 (d, 1H); 7.35 (d, 1H).
(2S,4S)-1-(4-Nitrobenzyloxycarbonyl)-2-(4-allyloxycarbonyl-2-thienylcarbamoyl)pyrrolidin- 4-ylthioacetate (diisopropylethylamine salt).

The title compound was prepared from allyl 2-amino-4-thiophenecarboxylate using a similar method to that of example 1, except allyl 2-amino-4-thiophenecarboxylate was solubilized in dichloromethane with diisopropylethylamine as described in example 2.

NMR (DMSO-$d_6$): δ1.9 (m, 1H); 2.35 (s, 3H); 2.75 (m, 1H); 3.25 (m, 1H); 3.85–4.25 (m, 2H); 4.5 (m, 1H); 4.65–4.85 (m, 2H); 5.05–5.5 (m, 4H); 6.0 (m, 1H); 6.9–8.4 (m, 6H).
Allyl (1R,5S,6S,8R,2'S,4'S)-2-(1-(4-nitrobenzyloxycarbonyl)-2-(4 -allyloxycarbonyl-2-thienylcarbamoyl)pyrrolidin- 4-ylthio)-6-(1 -hydroxyethyl)-1-methylcarbapenem-3-carboxylate.

The title compound was prepared from (2S,4S)-1-(4-nitrobenzyloxycarbonyl)- 2-(4-allyloxycarbonyl-2-thienylcarbamoyl) pyrrolidin- 4-ylthio acetate using a similar method to that of example 2.

NMR (DMSO-$d_6$+AcOD-$d_4$): δ1.15 (2d, 6H); 1.9 (m, 1H); 2.8 (m, 1H); 3;25 (dd, 1H); 3.35 (m, 1H); 3.55 (m, 1H); 3.9–4.05 (m, 2H); 4.2 (m, 1H); 4.4–4.75 (m, 5H); 5.0–5.4 (m, 6H); 5.8–6.1 (m, 1H); 7.4–8.3 (m, 6H).

EXAMPLE 4

(1R,5S,6S,8R,2'S,4'S)-2-(2-(3-Carboxy-2-(4,5,6,7)-tetrahydrobenzo(b)-thienylcarbarbamoyl)pyrrolidin- 4-ylthio)-6-(1-hydroxyethyl)-1-methylcarbapenem- 3-carboxylic acid (dipotassium salt).

The title compound was prepared from allyl (1R,5S,6S, 8R,2'S,4'S)- 2-(1-(4-nitrobenzyloxycarbonyl)-2-(3-carboxy-2-(4,5,6,7)-tetrahydrobenzo[ b]thienylcarbamoyl)pyrrolidin-4-ylthio)-6-(1-hydroxyethyl)- 1-methylcarbapenem-3-carboxylate diisopropylethylamine salt using a similar method to that of example 2.

NMR (DMSO-$d_6$+AcOD-$d_4$): δ1.15 (2d, 6H); 1.60–1.85 (m, 4H); 2.4–2.85 (m, 6H); 3.18 (dd, 1H); 3.3–3.65 (m, 3H); 3.88–4.1 (m, 2H); 4.15 (dd, 1H).

(2S,4S)-1-(4-Nitrobenzyloxycarbonyl)-2-(3-carboxy-2-(4, 5,6,7,-tetrahydrobenzo[ b]thienylcarbamoyl)pyrrolidin-4-ylthioacetate The title compound was prepared from 2-amino-3-carboxy- 4,5,6,7-tetrahydrobenzo[b]thiophene using a similar method to that of example 2.

NMR (DHSO-d6+AcOD-$d_4$): δ1.62–1.82 (m, 4H); 2.15 (m, 1H); 2.5–2.9 (m, 5H); 3.45 (m, 1H); 3.95–4.25 (m, 2H); 4.6 (dd, 1H); 5.15 (m, 1H); 5.37 (d, 1H); 7.5 (d, 2H); 8.05 (d, 2H).

Allyl (1R,5S,6S,8R,2'S,4'S)2-(1-(4-nitrobenzyloxycarbonyl)-2 -(3-carboxy-2-(4,5,6,7)-tetrahydrobenzo[b]thienylcarbamoyl)pyrrolidin- 4-ylthio)-6-(1-hydroxyethyl)-1-methylcarbapenem-3-carboxylate (diisopropylethylamine salt).

The title compound was prepared from allyl (1R,5R,6S, 8R)-6 -(1-hydroxyethyl)-1-methyl-2-diphenylphosphoryloxycarbapenem-3-carboxylate and (2S,4S)-1-(4-nitrobenzyloxycarbonyl)-2-(3-carboxy-2 -(4,5,6,7)-tetrahydrobenzo[b]thienylcarbamoyl)pyrrolidin-4-ylthiol using a similar method to that of example 1.

NMR (DMSO-$d_6$+AcOD-$d_4$): δ1.15 (2d, 6H); 1.7 (s, 4H); 2.05 (m, 1H); 2.65 (s, 4H); 3.25 (dd, 1H); 3.3–4.75 (m, 10H); 4.9–5.45 (m, 4H); 5.75 (m, 1H); 7.1–8.35 (m, 4H).

EXAMPLE 5

(1R,5S,6S,8R,2'S,4'S)-2-(2-(3-Carboxy-4-methyl-2 -thienylcarbamoyl)pyrrolidin- 4-ylthio)-6-(1-hydroxyethyl)-1-methylcarbapenem-3-carboxylic acid (dipotassium salt).

The title compound was prepared from allyl (1R,5S,6S, 8R,2'S,4'S)- 2-(1-(4-nitrobenzyloxycarbonyl)-(2-(3-carboxy-4-methyl-2 -thienylcarbamoyl)pyrrolidin-4-ylthio)-6-(1-hydroxyethyl)-1-methylcarbapenem carboxylate diisopropylethylamine salt using a similar method to that of example 2.

NMR (DMSO-$d_6$+AcOD $d_4$): 1.15 (2d, 6H); 1.7 (m, 1H); 2.32 (s, 3H); 2.52 (m, 1H); 2.67 (m, 1H); 3.18 (dd, 1H); 3.19 (m, 1H); 3.50 (m, 2H); 3.95 (m, 1H); 4.02 (m, 1H); 4.15 (dd, 1H); 6.55 (s, 1H).

(2S,4S)-1-(4-Nitrobenzyloxycarbonyl)-2-(3-ethoxycarbonyl-4-methyl-2 -thienylcarbamoyl)pyrrolidin-4-ylthioacetate.

The title compound was prepared from ethyl 2-amino-4-methyl- 3-thiophenecarboxylate using a similar method to that of example 2 except the ethyl 2-amino-4-methyl-3-thiophenecarboxylate was dissolved in dichloromethane in the presence of diisopropylethylamine.

NMR (CDCl$_3$): δ1.35 (m, 3H); 2.2 (m, 1H); 2.35 (2s, 6H); 2.82 (m, 1H); 3.52 (m, 1H); 4.0 (m 1H); 4.12–4.4 (m, 3H); 4.4–4.7 (m, 1H); 4.9–5.5 (m, 2H); 6.42 (s, 1H); 7.2–8.3 (m, 4H).

(2S,4S)-1-(4-Nitrobenzyloxycarbonyl)-2-(3-carboxy-4-methyl-2 -thienylcarbamoyl)pyrrolidin-4-ylthiol (2S,4S)-1-(4-Nitrobenzyloxycarbonyl)-2-(3-ethoxycarbonyl- 4-methyl-2-thienylcarbamoyl)pyrrolidin-4-ylthioacetate (0.86 g, 1.6 mmol) in dioxan (10 ml) and water (5 ml) was treated with 1M NaOH (5 ml, 4.8 mmol) for 3 hours at 60°. The reaction mixture was neutralised with 6M HCl to pH6, at 0°. The precipitated white solid was filtered off, washed with water and dried under vacuum.

Allyl (1R,5S,6S,8R,2'S,4'S)-2-(1-(4-nitrobenzyloxycarbonyl)-2-(3 -carboxy-4-methyl-2-thienylcarbamoyl)pyrrolidin-4-ylthio)-6-(1 -hydroxyethyl)-1-methylcarbapenem-3-carboxylate (diisopropylethylamine salt).

The title compound was prepared from allyl (1R,5R,6S, 8R)-6 -(1-hydroxyethyl)-1-methyl-2-diphenylphosphoryloxycarbapenem-3-carboxylate and (2S,4S)-1-(4-nitrobenzyloxycarbonyl)-2-(3-carboxy-4 -methyl-2-thienylcarbamoyl)pyrrolidin-4-ylthiol using a similar method to that of example 1.

NMR (DMSO-$d_6$+AcOD-$d_4$) 1.15 (m, 6H); 2.05 (m, 1H); 2.15 (m, 3H); 2.9 (m, 1H); 3.12 (dd, 1H); 3.4–3.6 (m, 2H); 3.9–4.15 (m, 2H); 4.42 (m, 2H); 4.6 (m, 3H); 5.0–5.4 (m, 4H); 5.6–6.05 (m, 1H); 6.62 (m, 1H); 7.2–8.3 (m, 4H).

EXAMPLE 6

(1R,5S,6S,8R,2'S,4'S)-2-(2-(2-Carboxy-5-thienylcarbamoyl)pyrrolidin- 4-ylthio)-6-(1-hydroxyethyl)-1-methylcarbapenem-3-carboxylic acid, dipotassium salt.

To a solution of 4-nitrobenzyl (1R,5S,6S,8R,2'S,4'S)-2 -(1-(4-nitrobenzyloxycarbonyl)-2-(2-allyloxycarbonyl-5-thienylcarbamoyl)pyrrolidin- 4-ylthio)-6-(1-hydroxyethyl)-1-methylcarbapenem-3-carboxylate (1 g, 1.2 mmol) in a mixture of methylene chloride (5 ml) and ethyl acetate (5 ml) were added triphenylphosphine (32 mg, 0.12 mmol), tetrakis triphenylphosphine palladium (48 mg, 0.04 mmol) and a 0.4M solution of potassium 2-ethyl hexanoate in ethyl acetate (3.5 ml, 1.38 mmol). The reaction mixture was stirred at ambient temperature for 1 hour, diluted with ethyl acetate and the precipitate filtered off, washed with ether and dried under vacuum. The crude acid was dissolved in a solution of water (30 ml) containing potassium hydrogen carbonate (132 mg, 1.32 mmol) and mixed with 10% palladium on charcoal (0.5 g). The mixture was stirred under a hydrogen atmosphere for 2 hours. The catalyst was filtered off, the organic phase discarded, the aqueous phase partially concentrated and purified by reverse phase chromatography (Nucleosil $C_{18}$10μ, 3.5×20 cm) with water as eluent to give after freeze drying the title compound (183 mg, 27%).

NMR (DMSO-$d_6$, AcOD-$d_4$): δ1.15 (d, 3H); 1.17 (d, 3H); 1.75 (m, 1H); 2.63 (m, 1H); 2.76 (m, 1H); 3.20 (dd, 1H); 3.34–3.43 (m, 2H); 3.64 (m, 1H); 3.94–4.02 (m, 2H); 4.15 (dd, 1H); 6.87 (d, 1H); 7.49 (d, 1H). MS (FAB+ve): 482 (M+H)$^+$; 520 (M+K)$^+$.

The starting materials were prepared as follows:
5-Nitro-2-thiophenecarboxylic acid.

The title compound was obtained starting from 2-thiophenecarboxylic acid, simultaneously with 4-nitro-2-thiophenecarboxylic acid described previously in example 1.

NMR (CDCl$_3$): δ7.65 (d, 1H); 7.88 (d, 1H).

Allyl 5-Nitro-2-thiophenecarboxylate

To a solution of 5-nitro-2-thiophenecarboxylic acid (20 g, 0.11 mol) in DMF (140 ml) were added sequentially allyl bromide (40 ml, 0.46 mol) and triethylamine (64 ml, 0.46 mol) with cooling to maintain the temperature of the reaction mixture below 30° C. After addition of the reagents, the reaction mixture was stirred for 3 hours at ambient temperature and then diluted with ethyl acetate. The solid which precipitated was filtered off, the filtrate washed with water, washed with saturated aqueous solution of sodium chloride, dried over MgSO$_4$ and concentrated. The residue was purified by chromatography on silica gel using a mixture of CH$_2$Cl$_2$-petroleum ether (3:7) as eluent to give the title compound as a white solid (8.8 g, 38%).

NMR (CDCl$_3$): δ4.84 (d, 2H); 5.36–5.45 (m, 2H); 6.00 (m, 1H); 7.71(d, 1H); 7.88 (d, 1H).

Allyl 5-amino-2-thiophenecarboxylate

To a solution of allyl 5-nitro-2-thiophenecarboxylate (3.2 g, 15 mmol) in concentrated hydrogen chloride (35 ml) was added, under cooling, SnCl$_2$.H$_2$O (10.1 g, 45 mmol). The mixture was stirred for 3.5 hours at ambient temperature, diluted with ethyl acetate and basified to pH 10 with 5N NaOH. The organic layer was washed with water and a saturated aqueous solution of sodium chloride, dried over MgSO$_4$ and concentrated. The residue was purified by chromatography on silica gel using a mixture of ethyl acetate and petroleum ether (3:7) to give the title compound as a yellow oil (1.94 g, 72%).

NMR (CDCl$_3$): δ4.34 (br s, 2H); 4.73 (d, 2H); 5.23 (d, 1H); 5.36 (d, 1H); 5.99 (m, 1H); 6.09 (d, 1H); 7.48 (d, 1H).

(2S,4S)-1-(4-Nitrobenzyloxycarbonyl)-2-(2-allyloxycarbonyl-5-thienylcarbamoyl)pyrrolidine- 4-ylthioacetate.

To a solution of (2S,4S)-4-acetylthio-2-carboxy-1-(4-nitrobenzyloxycarbonyl)pyrrolidine (3.79 g, 10.3 mmol) in CH$_2$Cl$_2$ (12 ml) were added thionyl chloride (3.75 ml, 51.5 mmol) and DMF (0.055 ml). The mixture was stirred for 16 hours at ambient temperature, concentrated and the residual oil taken up in CH$_2$Cl$_2$-toluene and reevaporated. The residue was dried under vacuum and solubilised in CH$_2$Cl$_2$ (25 ml). To this solution cooled to 0° C. was added N-diisopropylethylamine (2.05 ml, 11.8 mmol) and a solution of allyl 5-amino-2-thiophenecarboxylate (1.9 g, 10.3 mmol). After 15 minutes at ambient temperature, the solvent was evaporated and the residue taken up in a mixture of water and ethyl acetate. The organic layer was dried over MgSO$_4$ and evaporated to dryness. The residue was purified by chromatography on silica gel using a mixture of CH$_2$Cl$_2$-ether (9:1) to give the title compound as a yellow foam (4.68 g, 85%).

NMR (DMSO-d$_6$+AcOD-d$_4$): δ2.33 (s, 3H); 2.80 (m, 1H); 3.38 (m, 1H); 4.00–4.15 (m, 2H); 4.52 (m, 2H); 4.77 (d, 2H); 5.02–5.42 (m, 4H); 6.00 (m, 1H); 6.77 (m, 1H); 7.45 (m, 1H); 7.60–7.68 (m, 2H); 7.95 (m, 1H); 8.23 (m, 1H).

(2S,4S)-1-(4-Nitrobenzyloxycarbonyl)-2-(2-allyoxycarbonyl-5-thienylcarbamoyl)pyrrolidin- 4-ylthiol.

To a solution of (2S,4S)-1-(4-nitrobenzyloxycarbonyl)-2 -(2-allyloxycarbonyl-5-thienylcarbamoyl)pyrrolidin-4-ylthioacetate (1.06 g, 2 mmol) in dichloromethane (2 ml) was added at 0° C. ethanol (4 ml) followed by a 5N solution of methylamine in ethanol (0.8 ml, 4 mmol). The reaction mixture was stirred at ambient temperature for 1.5 hours and acidified to pH4 with 6N HCl. Ethyl acetate was added to the solution, the organic layer was washed with water and aqueous solution of sodium chloride, dried over MgSO$_4$ and evaporated to give the title compound as a yellow foam (0.96 g, 97%).

NMR (DMSO-d$_6$-TFA): δ1.87 (m, 1H); 2.73 (m, 1H); 3.29 (m, 1H); 3.44 (m, 1H); 4.01 (m, 1H); 4.42 (m, 1H); 4.72 (br s, 2H), 5.02–5.40 (m, 4H); 6.01 (m, 1H); 7.76 (m, 1H); 7.43 (d, 1H); 7.61–7.68 (m, 2H); 7.93 (d, 1H); 8.25 (d, 1H).

4-Nitrobenzyl (1R,5S,6S,8R,2'S,4'S)-2-(1-(4-nitrobenzyloxycarbonyl)- 2-(2-allyloxycarbonyl-5-thienylcarbamoyl)pyrrolidin-4-ylthio)-1 -hydroxyethyl)-1-methylcarbapenem-3-carboxylate.

To a solution of 4-nitrobenzyl (1R,5S,6S,8R)-6-(1-hydroxyethyl)- 1-methyl-2-diphenylphosphoryloxycarbapenem-3-carboxylate (940 mg, 1.9 mmol) in acetonitrile (10 ml) were added sequentially N-diisopropylethylamine (0.33 ml, 1.9 mmol), (2S,4S)-1-(4-nitrobenzyloxycarbonyl)- 2-(2-allyloxycarbonyl-5-thienylcarbamoyl)pyrrolidin- 4-ylthio (1 g, 1.9 mmol), in tri-n-butylphosphine (0.095 ml, 0.38 mmol) and water (0.03 ml). The reaction mixture was kept at 4° C. overnight, evaporated to dryness and the residue was purified by chromatography on silica gel using a mixture of CH$_2$Cl$_2$—CH$_3$CN (7:3) to give the title compound as a yellow foam (1.03 g, 72%).

NMR (DMSO-d$_6$-AcOD-d$_4$): δ1.17 (d, 3H); 1.19 (d, 3H); 1.95 (m, 1H); 2.83 (m, 1H); 3.30–3.62 (m, 3H); 3.96–4.30 (m, 4H); 4.47–4.60 (dt, 1H); 4.73 (br s, 2H); 5.03–5.44 (m, 6H); 6.00 (m, 1H); 6.77 (dd, 1H); 7.44 (d, 1H); 7.61 (dd, 1H); 7.67 (d, 1H); 7.7 (d, 2H); 7.94 (d, 1H); 8.21 (d, 1H); 8.24 (d, 2H).

EXAMPLE 7

(1R,5S,6S,8R,2'S,4'S)-2-(5-Carboxy-3,-hydroxy-2 -thienylcarbamoyl)pyrrolidine- 4-ylthio)-6-(1-hydroxyethyl)-1-methylcarbapenem-3-carboxylic acid.

A solution of sodium (1R,5S,6S,8R,2'S,4'S)-2-(1-(4-nitrobenzyloxycarbonyl)- 2-(-5-carboxy-3-hydroxy-2-thienylcarbamoyl)pyrrolidin- 4-ylthio)-6-(1-hydroxyethyl)-1-methylcarbapenem-3-carboxylate (92 mg, 0.13 mmol) in water (5 ml) and sodium bicarbonate (pH adjusted to 7.5) was hydrogenated at atmospheric pressure in presence of Pd/C (10%) (45 mg). The reaction was followed by analytical HPLC and took about 45 minutes. The catalyst was filtered off and the aqueous solution concentrated, and purified by preparative HPLC (Nucleosil C-18), eluting with water. Freeze drying the appropriate fractions gave the title compound (30 mg, 42%).

NMR: (DMSO-d$_6$+AcOD-d$_4$): δ1.15 (m, 6H); 1.7 (m, 1H); 2.65 (m, 2H); 3.2 (dd, 1H); 3.45 (m, 2H); 3.6 (m, 1H); 3.95 (dq, 1H); 4.05 (t, 1H); 4.15 (dd, 1H); 7.18 (s, 1H).

The starting material was prepared as follows:

tert-Butyl 3-tert-butoxy-2-ethyloxycarbonyl-5-thiophenecarboxylate

A solution of ethyl-3-hydroxy-5-carboxy-2-thiophenecarboxylate( 25 g, 0.115 mmol) in dry (25 g, 0.115 mmol) in dry CH$_2$Cl$_2$ (200 ml) was treated, at ambient temperature, with diisopropyl-tert-butylisourea (175 ml) added dropwise. This caused an exotherm which heated the mixture to reflux. The reaction mixture was then stirred for 12 hours, the solid removed by filtration, and the CH$_2$Cl$_2$ evaporated. The residual oil was purified by subjecting to silica gel chromatography, eluting with petroleum ether: ether (90:10) to give a mixture of two products (28.5 g). These two products were separated by flash chromatography, eluting with CH$_2$Cl$_2$: petroleum ether (1:1), to give title compound (12.6 g, 33%).

NMR: (DMSO-d$_6$): δ1.29 (t, 3H); 1.36 (s, 9H); 1.53 (s, 9H); 4.25 (q, 2H); 7.41 (s, 1H).

tert-Butyl-3-tert-butoxy-2-carboxy-5-thiophenecarboxylate

A solution of tert-butyl-3-tert-butoxy-2-ethyloxycarbonyl-5 -thiophenecarboxylate (11.5 g, 35 mmol) in dioxane with NaOH (2N) (34.5 ml, 70 mmol) was heated for 1.45 hours at 50° C. The mixture was cooled to 0° C., neutralized with HCl (2N), and the solvent evaporated. The residue was triturated with a concentrated aqueous solution of $Na_2CO_3$ (400 ml) and ether (200 ml). The aqueous phase was recovered, cooled to 0° C., acidified with HCl (5N) and extracted with ether. After drying, concentration of the etheral phase, and purification by flash silica gel chromatography, the title compound was obtained (3.45 g).

NMR: ($CDCl_3$): δ1.55 (s, 9H); 1.58 (s, 9H); 7.5 (s, 1H).

tert-Butyl-2-azidocarbonyl-3-tert-butoxy-5-thiophenecarboxylate

A solution of tert-butyl-2-carboxy-3-tert-butoxy-5-thiophenecarboxylate (3 g, 0.01 mmol) in dry acetone (100 ml) was treated, at 0° C., with triethylamine (1.7 ml, 0.012 mmol) added dropwise. The mixture was stirred for 15 minutes and ethyl chloroformate (1.25 ml, 0.013 mmol) added dropwise, at 0° C. After 30 minutes, sodium azide (1.1 g, 0.017 mmol) in water (5 ml) was slowly added, at 0° C. After 4 hours, stirring at ambient temperature, the reaction mixture was filtered and the solvent evaporated. The oily residue was dissolved in $CH_2Cl_2$, and the solution washed (2×) with water, dried over $MgSO_4$ and the solvent evaporated to give title compound (3.25 g, 100%).

NMR: (DMSO-$d_6$): δ1.50 (s, 9H); 1.60 (s, 9H); 7.45 (s, 1H).

tert-Butyl-2-allyloxycarbonylamino-3-tert-butoxy-5-thiophenecarboxylate

A solution of tert-butyl-2-azidocarbonyl-3-tert-butoxy-5-thiophenecarboxylate (1.5 g, 4.6 mmol) in allyl alcohol (0.5 ml, 7.3 mmol) and dry toluene (15 ml) was heated at 100° for 30 minutes, until evolution of nitrogen stopped. The mixture was evaporated, and the residue purified by subjecting to flash chromatography over silica gel, eluting with petroleum ether: ether (4:1) to give the title compound (1.64 g, 100%).

NMR: ($CDCl_3$): δ1.28 (s, 9H); 1.49 (s, 9H); 4.66 (m, 2H); 5.25–5.37 (m, 1H); 6.0 (m, 1H); 7.25 (m, 1H).

tert-Butyl-2-amino-3-tert-butoxy-5-thiophenecarboxylate

A solution of tert-butyl-2-allyloxycarbonylamino-3-tert-butoxy- 5-thiophenecarboxylate (1.64 g, 4.62 mmol) in anhydrous THF (50 ml) was treated with $PPh_3$ (240 mg, 0.923 mmol), dimedone (1.3 g, 9.23 mmol) and $Pd(PPh_3)_4$ (300 mg, 0.277 mmol). After 30 minutes, the solvent was evaporated, and the residue purified by flash silica-gel chromatography, eluting with petroleum ether: ether (80:20), to give the title compound (975 mg, 98%).

NMR: (DMSO-$d_6$): δ1.24 (s, 9H); 1.45 (s, 9H); 6.0 (s, 2H); 7.08 (s, 1H).

(2S,4S)-1-(4-Nitrobenzyloxycarbonyl)-2-(3-tert-butoxy-5-tertbutyloxycarbonyl- 2-thienylcarbamoyl)pyrrolidin-4-ylthioacetate.

(2S,4S)-1-(4-Nitrobenzyloxycarbonyl)-4-acetylthio-2-carboxypyrrolidine (1.5 g, 4 mmol) was solubilized in dry $CH_2Cl_2$ (15 ml) and treated with thionylchloride (1.5 ml, 20 mmol) and a catalytic amount of DMF (20 ml). The mixture was stirred for 12 hours at ambient temperature, the solvent evaporated, and the residual oil, dried under vacuum for 2 hours, solubilized in $CH_2Cl_2$ (15 ml) and added to a solution of tert-butyl-2-amino-3-tert-butoxy-5-thenoate (1.1 g, 4 mmol) in $CH_2Cl_2$ (15 ml) and diisopropylethylamine (0.85 ml, 4.9 mmol), at 0° C. The mixture was stirred for 30 minutes, the solvent evaporated, and the residue purified by flash silica gel chromatography, eluting with petroleum ether: ether (20:80), to give the title compound (2.17 g, 85%).

NMR: ($CDCl_3$): δ1.56 (s, 9H); 1.58 (s, 9H); 2.32 (s, 3H); 2.55 (m, 1H); 2.74 (m, 1H); 3.38 (m, 1H); 4.01 (m, 1H); 4.15 (m, 1H); 4.63 (m, 1H); 5.3 (m, 2H); 7.39 (s, 1H); 7.52 (m, 2H); 8.22 (m, 2H).

(2S,4S)-1-(4-Nitrobenzyloxycarbonyl)-2-(3-hydroxy-5-carboxy-2 -thienylcarbamoyl)pyrrolidin-4-ylthiol.

(2S,4S)-1-(4-Nitrobenzyloxycarbonyl)-2-(3-tert-butoxy-5-tert-butyloxycarbonyl- 2-thienylcarbamoyl)pyrrolidin-4-ylthioacetate (1 g, 1.6 mmol) was solubilized in $CH_2Cl_2$ (2 ml) and dry ethanol (5 ml) and treated with a solution of methylamine (4.24M) in ethanol (1.15 ml, 4.83 mmol). The progress of the reaction was monitored by tlc. After 1.5 hours, the mixture was evaporated, the residue solubilized in $CH_2Cl_2$ (5 ml) and treated with TFA (5 ml) for 1.5 hours, at ambient temperature. The solvent was evaporated and the residue triturated with ether to give title compound (1.1 g, 100%).

NMR: (DMSO-$d_6$): δ1.8 (m, 1H); 2.7 (m, 1H); 3.4 (m, 1H); 4.00 (m, 2H); 4.62 (m, 1H); 5.00–5.26 (m, 2H); 7.16 (m, 1H), 7.45 (m, 1H), 7.65 (m, 1H); 7.94 (m, 1H); 8.23 (m, 1H).

Allyl (1R,5R,6S,8R,2'S,4'S)-2-(1-(4-nitrobenzyloxycarbonyl-2-(3 -hydroxy-5-carboxy-2-thienylcarbamoyl)pyrrolidin-4-ylthio)-6-(1 -hydroxyethyl)-1-methylcarbapenem-3-carboxylate.

A solution of allyl (1R,5R,6S,8R)-6-(1-hydroxyethyl)-1 -methyl-2-diphenylphosphoryloxycarbapenem-3-carboxylate (800 mg, 1.6 mmol) in DMF (8 ml) under argon was treated with (2S,4S)-1-(4 -nitrobenzyloxycarbonyl)-2-(3-hydroxy-5-carboxy-2-thienylcarbamoyl)pyrrolidin-4-ylthiol (752 mg, 1.6 mmol), diisopropylethylamine (0.835 ml, 4.8 mmol), tributylphosphine (200 μl, 0.8 mmol) and water (15 ml, 0.8 mmol), for 12 hours at ambient temperature. The mixture was then purified by subjecting to chromatography on a HP20SS column, eluting with a gradient of acetonitrile, water to give title compound (286 mg, 25%).

NMR: (DMSO$d_6$+AcOD-$d_4$): δ1.1–1.3 (m, 6H); 1.85 (m, 1H); 2.75 (m, 1H); 3.25 (dd, 1H); 3.3 (m, 1H); 3.5–3.7 (m, 1H); 3.7–4.3 (m, 4H); 4.5–4.8 (m, 3H); 4.9–5.5 (m, 4H); 5.9 (m, 1H); 7.17 (m, 1H); 7.46 (m, 1H); 7.66 (m, 1H); 7.96 (m, 1H); 8.73 (m, 1H).

(1R,5R,6S,8R,2'S,4'S)-2-(1-(4-Nitrobenzyloxycarbonyl)-2-(3 -hydroxy-5 -carboxy-2-thienylcarbamoyl)pyrrolidin-4-ylthio)-6-(1-hydroxyethyl)-1 -methylcarbapenem-3-carboxylic acid.

A solution of allyl (1R,5R,6S,8R,2'S,4'S)-2-(1-(4-nitrobenzyloxycarbonyl)- 2-(3-hydroxy-5-carboxy-2-thienylcarbamoyl)pyrrolidin- 4-ylthio)-6-(1-hydroxyethyl)-1-methylcarbapenem-3-carboxylate (240 mg, 0.335 mmol) in DMF (4 ml) under argon, was treated with $Pd(PPh_3)_4$ (30 mg, 0.026 mmol) and Meldrum's acid (48 mg, 0.335 mmol). The mixture was stirred for 1 hour, at ambient temperature. The solvent was evaporated, the residue solubilized in water, the pH adjusted to 7.5 with $NaHCO_3$ and the solution purified by $C_{18}$ (Nucleosil) chromatography, eluting with water: $CH_3CN$ (gradient) to give the title compound, (92 mg, 39%).

NMR: (DMSO-$d_6$+AcOD-$d_4$): 1.15 (m, 6H); 1.85 (m, 1H); 2.5 (m, 1H) (under DMSO); 2.77 (m, 1H); 3.19 (dd, 1H); 3.25–3.5 (m, 1H); 3.8–4.2 (m, 3H); 4.6 (m, 1H); 4.7 (m, 1H); 5.0–5.3 (m, 2H); 7.15 (s, 1H); 7.46 (m, 1H); 7.67 (m, 1H); 7.97 (m, 1H); 8.24 (m, 1H).

I claim:

1. A compound of the formula (I):

$$\text{(I)}$$

structure of formula (I): R¹ substituent on β-lactam ring with R² (H above), fused to pyrroline with CO₂H; S-linked to pyrrolidine bearing NH and CON-R³-thienyl-CO₂H or a pharmaceutically acceptable salt or an in vivo hydrolysable ester thereof;
wherein:
$R^1$ is 1-hydroxyethyl, 1-fluoroethyl or hydroxymethyl;
$R^2$ is hydrogen or $C_{1-4}$alkyl;
$R^3$ is hydrogen or $C_{1-4}$alkyl;
and the thienyl ring is optionally further substituted by one or two substituents selected from halo, cyano, $C_{1-4}$alkyl, nitro, hydroxy, carboxy, $C_{1-4}$alkoxy, trifluoromethyl, $C_{1-4}$alkoxycarbonyl, amino, $C_{1-4}$alkylamino, di-$C_{1-4}$alkylamino, sulfonic acid, $C_{1-4}$alkylS(O)$_n$— wherein n is 0–2, $C_{1-4}$alkanoylamino, $C_{1-4}$alkanoyl(N-$C_{1-4}$alkyl)amino, carbamoyl, $C_{1-4}$alkylcarbamoyl, di-$C_{1-4}$alkylcarbamoyl and N-$C_{1-4}$alkanesulfonamido; or by a tetramethylene group attached to adjacent carbon atoms on the thienyl ring.

2. A compound according to claim 1 wherein $R^1$ is 1-hydroxyethyl.

3. A compound according to either claim 1 or claim 2 wherein $R^2$ is hydrogen or methyl.

4. A compound according to either claim 1 or claim 2 wherein $R^2$ is methyl.

5. A compound according to any one of claims 1 or 2 wherein $R^3$ is hydrogen.

6. A compound according to claim 1, of the formula (IV):

$$\text{(IV)}$$

wherein $R^3$ and optional substituents on the thienyl ring are as defined in claim 1.

7. A compound according to claim 6 wherein the thienyl ring is optionally substituted by halo, cyano, $C_{1-4}$alkyl, nitro, carboxy, hydroxy, $C_{1-4}$alkoxy, carbamoyl, amino, trifluoromethyl or tetramethylene.

8. A compound according to either claim 6 or claim 7 wherein $R^3$ is hydrogen and the thienyl ring is either not further substituted or substituted by one substituent selected from methyl or hydroxy or by tetramethylene.

9. A compound according to claim 1 selected from
(1R,5S,6S,8R,2'S,4'S)-2-(2-(2-carboxy-4-thienylcarbamoyl)pyrrolidin-4-ylthio)-6-(1-hydroxyethyl)-1-methylcarbapenem-3-carboxylic acid;
(1R,5S,6S,8R,2'S,4'S)-2-(2-(2-carboxy-3-thienylcarbamoyl)pyrrolidin-4-ylthio)-6-(1-hydroxyethyl)-1-methylcarbapenem-3-carboxylic acid;
(1R,5S,6S,8R,2'S,4'S)-2-(2-(4-carboxy-2-thienylcarbamoyl)pyrrolidin-4-ylthio)-6-(1-hydroxyethyl)-1-methylcarbapenem-3-carboxylic acid;
(1R,5S,6S,8R,2'S,4'S)-2-(2-(3-carboxy-2-(4,5,6,7)-tetrahydrobenzo[b]-thienylcarbamoyl)pyrrolidin-4-ylthio)-6-(1-hydroxyethyl)-1-methylcarbapenem-3-carboxylic acid;
(1R,5S,6S,8R,2'S,4'S)-2-(2-(3-carboxy-4-methyl-2-thienylcarbamoyl)pyrrolidin-4-ylthio)-6-(1-hydroxyethyl)-1-methylcarbapenem-3-carboxylic acid;
(1R,5S,6S,8R,2'S,4'S)-2-(2-(2-carboxy-5-thienylcarbamoyl)pyrrolidin-4-ylthio)-6-(1-hydroxyethyl)-1-methylcarbapenem-3-carboxylic acid; and
(1R,5S,6S,8R,2'S,4'S)-2-(2-(5-carboxy-3-hydroxy-2-thienylcarbamoyl)pyrrolidin-4-ylthio)-6-(-1-hydroxyethyl)-1-methylcarbapenem-3-carboxylic acid;
or a pharmaceutically acceptable salt thereof.

10. A pharmaceutical composition which comprises a compound according to any one of claims 1, 6 or 9 and a pharmaceutically acceptable carrier.

11. A method of treatment of a bacterial infection by administering an antibacterially effective amount of a compound of the claim 1 to a patient in need thereof.

12. A compound of the formula (V):

$$\text{(V)}$$

wherein:
$R^2$ is hydrogen or $C_{1-4}$alkyl;
$R^{10}$ is hydrogen or $C_{1-4}$alkyl or an amino protecting group;
$R^{13}$ is hydrogen or $C_{1-4}$alkyl, protected hydroxymethyl or 1-(protected hydroxy) ethyl;
$R^{11}$ is hydrogen or a carboxy protecting group;
$R^{12}$ is hydrogen or an amino protecting group;
$R^{18}$ is carboxy or a protected carboxy group;
and the thienyl ring is optionally further substituted by one or two substituents selected from halo, cyano, $C_{1-4}$alkyl, nitro, hydroxy, carboxy, $C_{1-4}$alkoxy, trifluoromethyl, $C_{1-4}$alkoxycarbonyl, amino, $C_{1-4}$alkylamino, di-$C_{1-4}$alkylamino, sulfonic acid, $C_{1-4}$alkylS(O)$_n$— wherein n is 0–2, $C_{1-4}$alkanoylamino, $C_{1-4}$alkanoyl (N-$C_{1-4}$alkyl) amino, carbamoyl, $C_{1-4}$alkylcarbamoyl, di-$C_{1-4}$alkylcarbamoyl and N-$C_{1-4}$alkanesulfonamido; or by a tetramethylene group attached to adjacent carbon atoms on the thienyl ring;
and wherein any functional group of an optional substitutent on the thienyl group is optionally protected.

* * * * *